US006981965B2

(12) United States Patent
Luther et al.

(10) Patent No.: US 6,981,965 B2
(45) Date of Patent: Jan. 3, 2006

(54) UNIVERSAL PASSIVE PROTECTOR FOR AN IV CATHETER

(75) Inventors: Ronald B. Luther, Newport Beach, CA (US); Tuan Pham, Garden Grove, CA (US); John Muri, Aliso Viejo, CA (US)

(73) Assignee: Luther Research Partners LLC, Costa Mesa, CA (US)

( * ) Notice: Subject to any disclaimer, the term of this patent is extended or adjusted under 35 U.S.C. 154(b) by 104 days.

(21) Appl. No.: 10/003,782

(22) Filed: Oct. 31, 2001

(65) Prior Publication Data

US 2003/0083620 A1 May 1, 2003

(51) Int. Cl.
A61M 5/00 (2006.01)

(52) U.S. Cl. .................... 604/110; 604/192; 604/198; 604/199

(58) Field of Classification Search ............... 604/110, 604/263, 197, 198, 192, 164.01, 162, 164.08, 604/164.09, 164.11, 164.12, 165.01, 165.02, 604/165.03, 93.01, 527, 264, 167.06
See application file for complete search history.

(56) References Cited

U.S. PATENT DOCUMENTS

| 4,747,831 | A | | 5/1988 | Kulli |
| 4,762,516 | A | | 8/1988 | Luther et al. |
| 4,790,828 | A | | 12/1988 | Dombrowski et al. |
| 4,950,252 | A | | 8/1990 | Luther et al. |
| 4,978,344 | A | | 12/1990 | Dombrowski et al. |
| 4,994,041 | A | | 2/1991 | Dombrowski et al. |
| 5,135,502 | A | * | 8/1992 | Koenig, Jr. et al. ......... 604/164 |
| 5,312,371 | A | | 5/1994 | Dombrowski et al. |
| 5,419,766 | A | | 5/1995 | Chang et al. |
| 5,531,701 | A | | 7/1996 | Luther |
| 5,599,310 | A | * | 2/1997 | Bogert ....................... 604/164 |
| 5,718,688 | A | | 2/1998 | Wozencroft |
| 5,865,806 | A | | 2/1999 | Howell |
| 5,891,098 | A | | 4/1999 | Huang |
| 5,957,893 | A | | 9/1999 | Luther et al. |
| 6,056,718 | A | | 5/2000 | Funderburk et al. |
| 6,090,078 | A | | 7/2000 | Erskine |
| 6,520,938 | B1 | * | 2/2003 | Funderburk et al. ... 604/164.08 |
| 6,595,954 | B1 | * | 7/2003 | Luther et al. ............... 604/110 |

* cited by examiner

Primary Examiner—Long V. Le
Assistant Examiner—Ann Y. Lam
(74) Attorney, Agent, or Firm—Knobbe Martens Olson & Bear LLP

(57) ABSTRACT

A universal passive protector for an IV catheter is provided. The protector comprises an over-the-needle catheter including a proximal hub. The hub is secured within a hub trap comprising first and second interlocking arms. The hub trap is secured to a distal end of a tubular sheath. A slider is disposed about the sheath, and connected to a proximal end of the needle through a slit in the sheath. When the slider is in a distal position, the needle maintains the arms in a closed configuration wherein the hub is secured to the hub trap. When the slider is moved to a proximal position, the needle moves to a proximal position wherein the needle no longer maintains the arms in a closed position. The arms snap to an open position, releasing the hub and trapping the sharp distal tip of the needle within the sheath. Medical technicians are thus protected against accidental needle sticks.

20 Claims, 15 Drawing Sheets

UNIVERSAL PASSIVE PROTECTOR FOR AN IV CATHETER

BACKGROUND OF THE INVENTION

1. Field of the Invention

The present invention relates to medical devices. More particularly, the present universal passive protector for an IV catheter relates to intravenous catheters designed to protect medical personnel from accidental impalement and possible infection.

2. Description of the Related Art

Medical professionals commonly use intravenous needles to insert and withdraw fluid from patients. However, when introducing or withdrawing large amounts of fluid, such that the intravenous device is disposed within the vein for an extended period of time, metal needles are disadvantageous because their rigid structure and sharp distal tip can cause trauma to the patient's vein. Thus, medical professionals commonly use a catheter for such applications.

A catheter typically comprises a flexible tube having a soft tip. Catheters are generally inserted into the patient's vein using a catheter introduction device. A first type of introduction device comprises a through-the needle catheter, which is inserted into an anatomical passage through the use of a cannula. The cannula itself typically comprises an elongate, metal needle which punctures the skin, tissue and vein wall to provide a path for placement of the catheter in the vein. When the needle pierces the vein, blood will "flashback" through the needle and into a flashback chamber typically located at the proximal end of the needle. Thus, once the medical technician observes this "flashback" of blood, the medical technician will know that the needle has been inserted into the vein. The catheter is then advanced through the interior of the needle and into the passage. Once the catheter is properly inserted into the passage, the needle is withdrawn from the patient and the catheter can be advanced further into the vein.

A second type of introduction device comprises an over-the-needle catheter system. In such over-the-needle catheter systems, a thin catheter having a hub attached to its proximal end is advanced over a rigid cannula, such as a needle, with the cannula and catheter being simultaneously inserted into a desired anatomical passage of a patient. Once the cannula and accompanying catheter have been introduced into the passage, which is typically indicated by a flashback chamber filling with blood, the cannula is withdrawn from within the catheter interior, thus leaving the catheter operatively disposed within the passage. Thereafter, a hub mounted to the proximal end of the catheter may be used to fluidly connect the same to an infusion line or device.

However, once the catheter has been inserted into the anatomical passage, the cannula can typically only be removed from therewithin by retracting the same upwardly along the catheter, thereby undesirably exposing both the patient and the attendant medical personnel to accidental contact with the cannula, and more particularly the piercing tip of the needle. In recent years, concern over such accidental needlesticks has become more pronounced because of the advent of currently incurable and fatal diseases, such as Acquired Immune Deficiency Syndrome ("AIDS"), which can be transmitted by the exchange of bodily fluids from an infected person to another person. A needle that has been used to place a catheter in the vein of an AIDS infected person is a vehicle for transmission of the disease. Thus, it is advantageous to cover a needle immediately after use to avoid needlesticks.

A number of protective devices have been developed recently to help reduce the incidence of disease transmission through needlesticks. Some of these devices comprise an elongate sheath into which the needle advances as it is withdrawn from the patient. When the needle is completely withdrawn, its sharp distal tip is safely enclosed within a wider tube, which is usually made of plastic. Generally, a locking mechanism prevents the needle from exiting the sheath.

U.S. Pat. Nos. 4,762,516 and 4,950,252 disclose examples of typical protective devices for use with an over-the-needle catheter. The devices described in these patents each comprise a hub attached to the proximal end of the catheter. A proximal end of the hub is in turn connected to a distal end of an elongate sheath via a friction fit. The sheath is a tube, usually plastic, having a rectangular cross-section and a hollow cavity enclosed by sidewalls. Other similar devices may have different cross-sections, such as round or octagonal. A slider disposed about the outside of the sheath is attached to the proximal end of the needle. The slider may be attached to the needle through a hole in a proximal end of the sheath, or through a longitudinal slit in a sidewall of the sheath. A proximal portion of the sheath includes a pair of oppositely-disposed outwardly-biased tabs. A distal portion of an inside surface of the slider includes a pair of indentations configured to matingly receive the tabs.

With the slider positioned about the distal end of the sheath, the sharp distal tip of the needle protrudes from the distal end of the catheter. After insertion of the needle into the patient's vein, the slider is moved toward the proximal end of the sheath, thereby drawing the needle out of the patient's vein and leaving the catheter disposed within the vein. As the slider nears the proximal end of the sheath, and the distal tip of the needle nears the distal end of the sheath, the inside surface of the slider maintains the tabs inwardly of the slider. As the distal tip of the needle enters the distal end of the sheath, the indentations on the inside surface of the slider reach the outwardly biased tabs on the sheath. The tabs snap into the indentations, locking the relative positions of the slider and sheath. The sharp distal tip of the needle is thus safely locked within the sheath. When the needle is safely stowed, the hub is removed from the sheath, and is ready to receive an injection/aspiration device.

Device like those described in the '516 and '252 patents, however, are prone to leaving the sharp distal tip of the needle exposed. The friction fit between the hub and the distal end of the sheath is unreliable. During catheter emplacement with one of these devices, the hub frequently disengages the sheath before the needle is completely retracted within the sheath. Of course, when the sharp needle tip exits the protective catheter before it enters the protective sheath, it could stick the operator or the patient.

Another type of protective device for use with an over-the-needle catheter is disclosed in U.S. Pat. Nos. 4,790,828, 4,978,344, 4,994,041 and 5,312,371. Devices of the type described in these patents comprise a needle assembly including a body or handle and an elongate needle extending from a distal end of the body. A cap, through which the needle passes, is secured to a distal end of the body, usually by a friction fit. A catheter hub is friction fit over the cap, and the catheter extends from a distal end of the hub and envelops the needle.

Upon inserting a distal tip of the catheter into a patient's vein, a medical professional grasps the catheter assembly and dislodges the friction fit between the cap and the body while withdrawing the needle from the catheter. The catheter hub and cap, which are friction fit together, thus move toward the distal tip of the needle. The cap pulls a capping mechanism, such as a tether cord or accordian-style sheath, along with it. When the cap reaches the distal tip of the needle, the capping mechanism becomes taut. Further withdrawal of the needle from the cap/catheter releases the friction fit between the cap and catheter hub. The cap thus covers the needle distal tip and the catheter is positioned in the patient's vein for use.

Like the devices described in the '516 and '252 patents, devices of the type described in the '828, '344, '041 and '371 patents cause needle sticks when the friction fit between the cap and catheter hub comes loose before the cap reaches the needle distal tip. These devices demonstrate that relying on a friction fit to prevent needle sticks is very risky. If the friction fit it too loose, the likelihood of a needle stick is high. If the friction fit is too tight, the device is difficult for a medical professional to manipulate.

U.S. Pat. Nos. 4,747,831 and 6,090,078 disclose examples of another type of protective device for use with an over-the-needle catheter. This type of device comprises a catheter having a hub attached to its proximal end. The needle is mounted at its proximal end to a piston. The piston is in turn mounted within a cylinder, which is a hollow plastic tube that is open at a distal end. The piston is biased toward a proximal end of the cylinder by a spring. In a pre-emplacement configuration, however, the piston is secured at the distal end of the cylinder by a latch attached to an external button. The needle thus protrudes from the distal end of the catheter.

After inserting the catheter into a patient's vein, a medical professional presses the button, releasing the spring and causing the needle to retract within the cylinder. The sharp distal tip of the needle is thus safely enclosed within the rigid plastic sheath. Depressing the button also releases the hub from the cylinder. The hub is thus ready to receive an injection/aspiration device.

Disadvantageously, devices of the type described in the '831 and '078 patents often malfunction. The button used to retract the needle is very sensitive. Thus, the medical professional often depresses the button accidentally before the catheter is properly emplaced. Such accidental activation is unlikely to result in a needle stick, but it usually causes the catheter to become contaminated. When the hub is released without the distal end of the catheter safely inserted into the patient's vein, the catheter is unrestrained and usually falls to the floor. Upon contact with the floor or other non-sterile surface, the catheter must be discarded. The operator must then perform the procedure again using a new device. Thus, these devices generate a great deal of waste, both of material and of time. Further, if the operator pierces the patient's skin before accidentally activating the device, the patient must endure multiple needle sticks in order to have a catheter emplaced in his or her vein.

U.S. Pat. No. 5,718,688 describes still another type of protective device for use with an over-the-needle catheter. The device comprises a catheter having an axial bore, a catheter hub at one end of the catheter, an introducing needle having a sharp distal tip, and a needle hub on the needle remote from the distal tip. Instead of an elongate plastic tube enclosing the entire needle, this device includes only a needle tip protector on the needle for shielding the needle tip when the needle has been withdrawn from the catheter bore. The needle tip protector includes a locking device which is initially in an unlocked position, permitting withdrawal of the needle from the catheter bore. Upon withdrawal of the needle from the catheter bore, the protector springs into a locked position, in which the locking device engages the outer surface of the needle and shields the sharp distal tip. The locking device retains the catheter hub on the needle when the locking device is in the unlocked position and releases the catheter hub from the needle when the locking device is in the locked position. Separation of the catheter from the needle is therefore prevented until the needle has been withdrawn from the catheter bore to trigger shielding of the needle tip.

Devices like the one described in the '688 patent, however, suffer from a number of drawbacks. First, these devices cover only the needle tip, and not the entire needle. During catheter insertion, however, portions of the needle other than the tip may become coated with blood. When exposed to medical personnel, this blood presents a safety hazard.

Second, these devices rely on friction to be effective. When the protector springs to the open position, locking cams engage the needle. The locking cams pinch the needle to secure the protector from being pulled off the distal end of the needle. The frictional force generated by the pinching locking cams, however, is relatively weak. Thus, the protector is rather easily pulled off the needle distal end, leaving the contaminated needle exposed.

Third, the protectors of these devices are very complex, and involve delicate moving parts. Consequently, they are difficult and expensive to manufacture, and prone to sudden failure. The embodiment of FIGS. 1 and 2, for instance, comprises a locking cam that is connected to one of the locking parts by a flexible hinge portion that is nothing more than a razor thin segment of plastic. A minor manufacturing defect in this critical portion of the protector could easily lead to failure and consequent exposure of medical personnel to a contaminated needle.

Thus, a passive protector for an IV catheter that is simply and cheaply constructed, completely encloses a used needle, and prevents needle sticks in a virtually foolproof manner without generating a large amount of waste, would be of great benefit to the healthcare profession.

SUMMARY OF THE INVENTION

The preferred embodiments of the universal passive protector for an IV catheter have several features, no single one of which is solely responsible for their desirable attributes. Without limiting the scope of this universal passive protector for an IV catheter as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include compatibility with any catheter hub, protection against needle sticks without the need to exercise extreme caution, and ease of operation for consistent proper catheter emplacement.

A preferred embodiment of the universal passive protector for an IV catheter comprises an over-the-needle catheter including a hub. The hub is retained within a hub trap comprising first and second arms. A slider connected to a proximal end of the needle is movable along a sheath from a distal position to a proximal position. When the slider is in the distal position, the needle extends through a locking structure of the hub trap, thereby retaining the first and second arms in a closed position wherein the hub is trapped between the first and second arms. When the slider is in the distal position, a distal tip of the needle is proximal of the locking structure and the first and second arms are in an open position wherein the hub is released from the hub trap. Further, when the arms are in the open position, the needle is blocked from reemerging from the sheath by interlocking fingers of the first and second arms. The protector thus ensures that the sharp tip of the needle is safely stowed before releasing the hub.

BRIEF DESCRIPTION OF THE DRAWINGS

The preferred embodiments of the universal passive protector for an IV catheter, illustrating its features, will now be discussed in detail. These embodiments depict the novel and non-obvious universal passive protector for an IV catheter shown in the accompanying drawings, which are for illustrative purposes only. These drawings include the following figures, in which like numerals indicate like parts.

DETAILED DESCRIPTION OF THE PREFERRED EMBODIMENTS

Figure 1A:
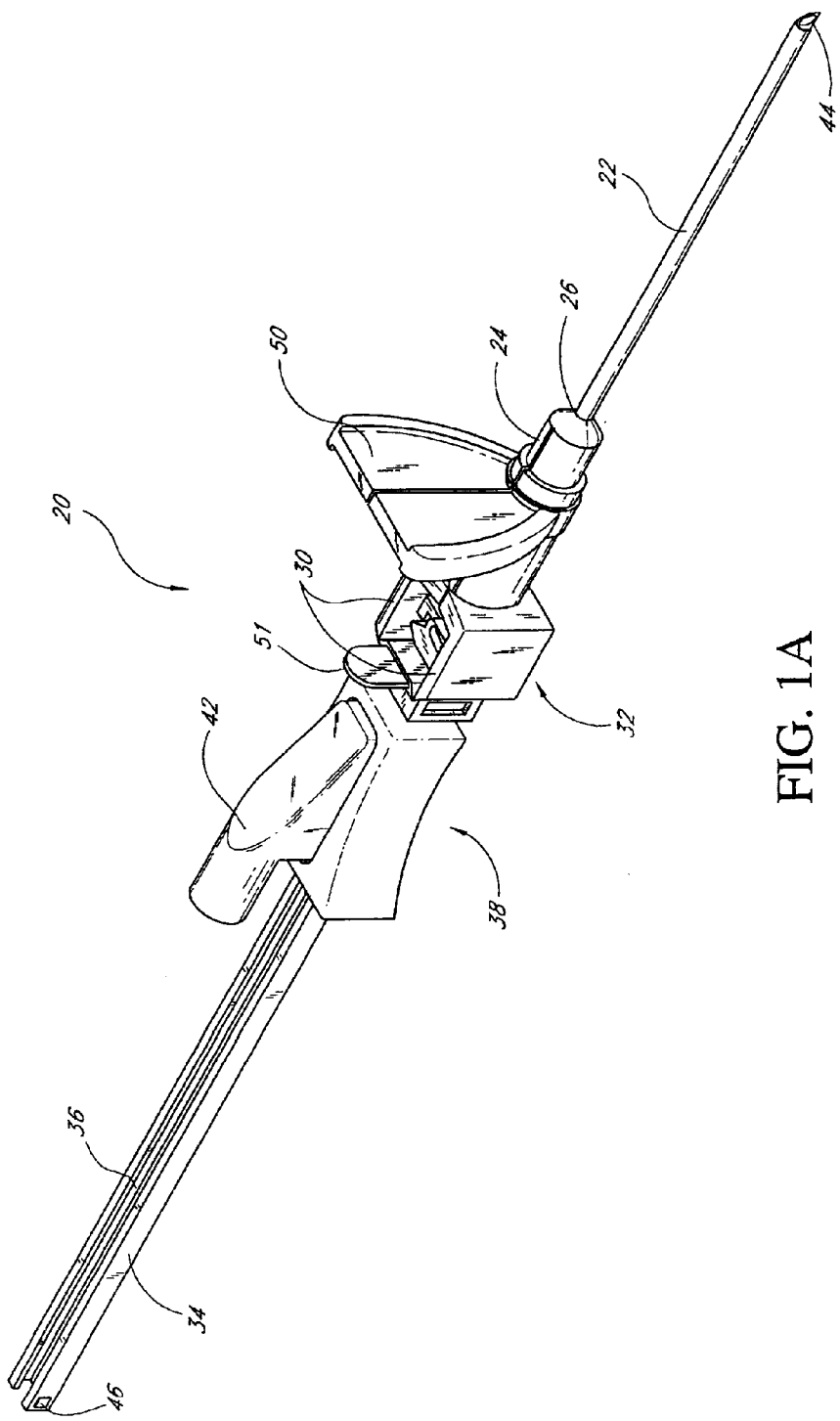
FIG. 1A is a perspective view of a preferred embodiment of the universal passive protector for an IV catheter according to the present invention, illustrating the arms in the closed position.
Figure 1B:
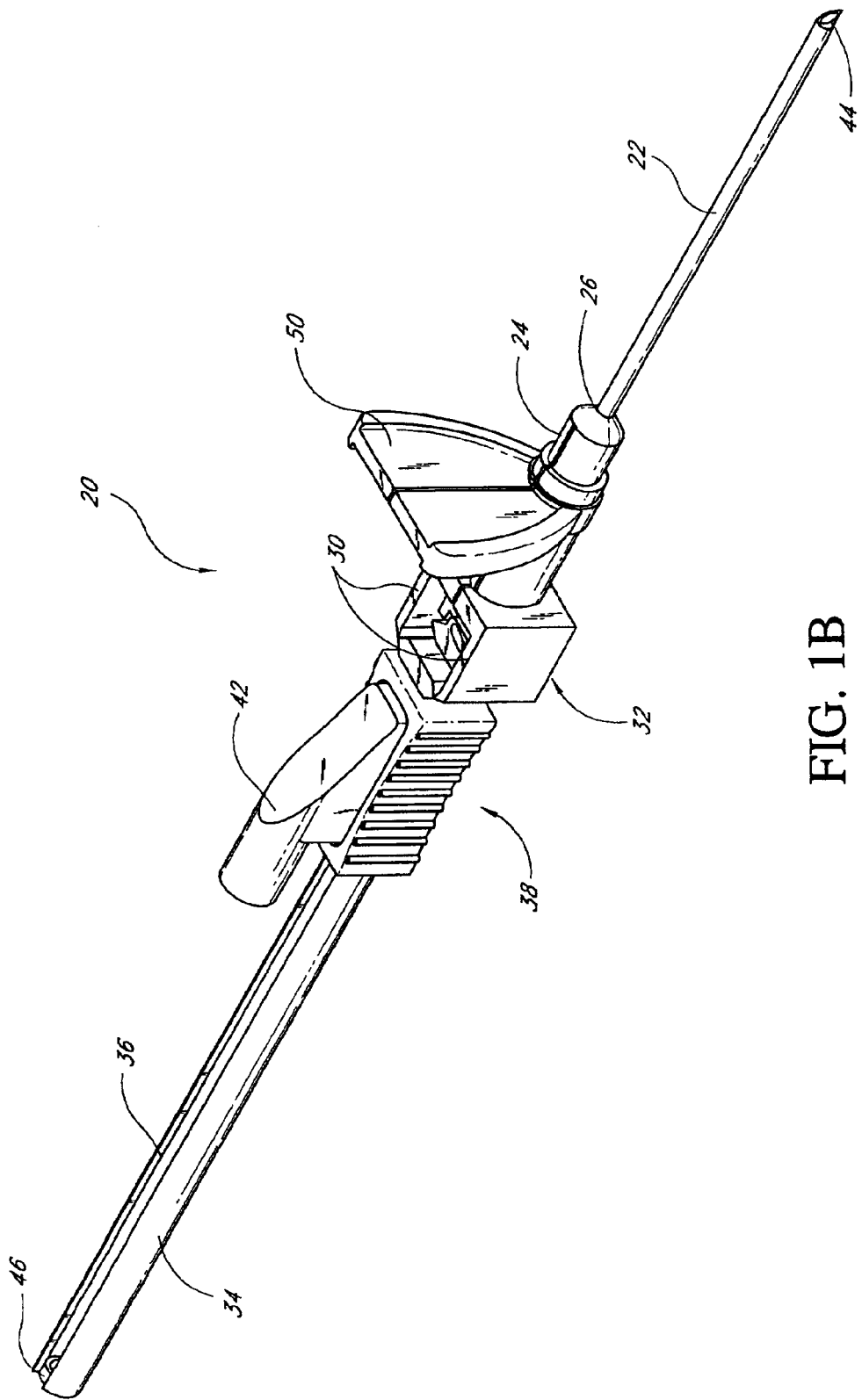
FIG. 1B is a perspective view of another preferred embodiment of the universal passive protector for an IV catheter, illustrating the arms in the closed position.
Figure 1C:
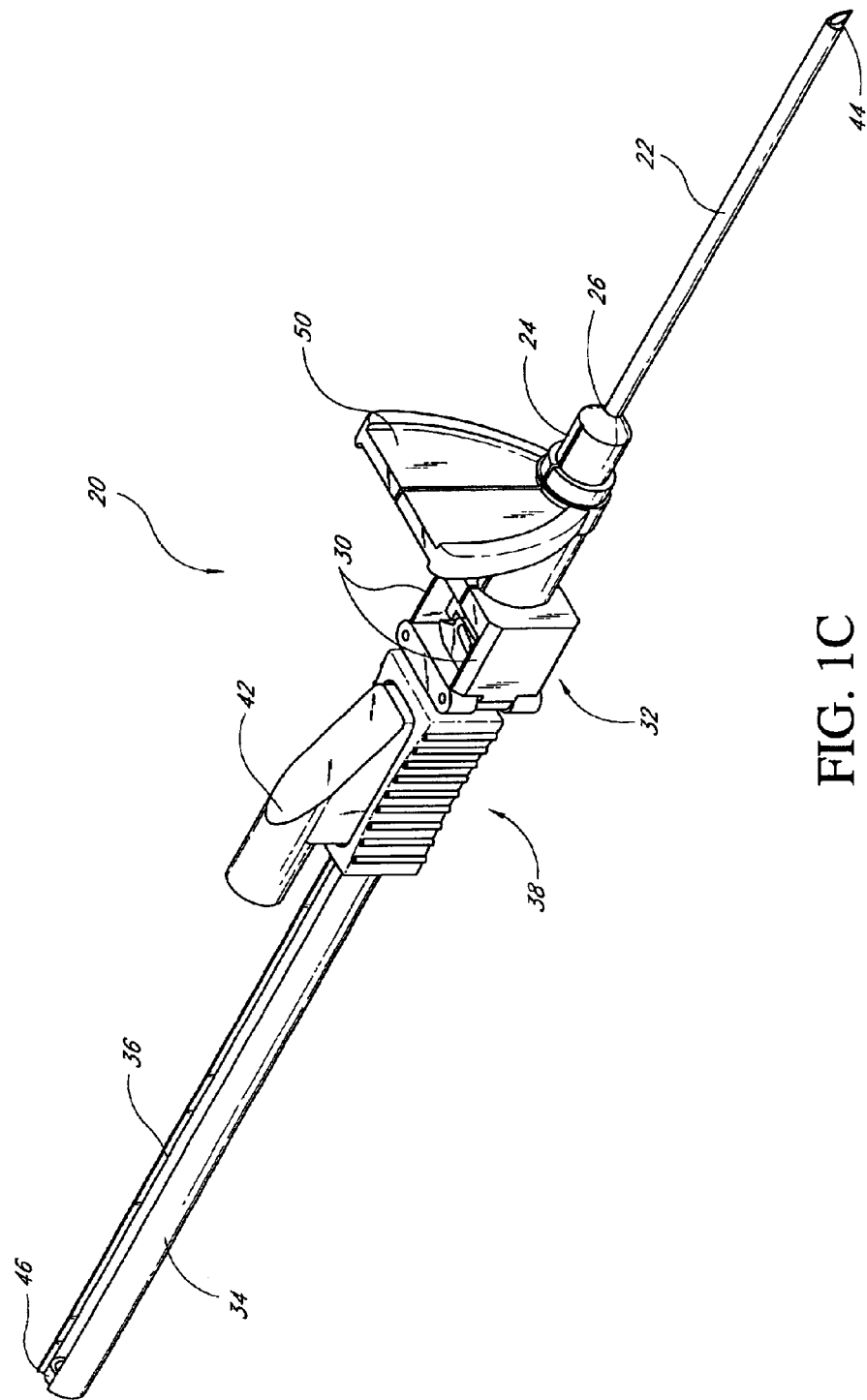
FIG. 1C is a perspective view of another preferred embodiment of the universal passive protector for an IV catheter, illustrating the arms in the closed position.

As FIGS. 1A, 1B and 1C illustrate, preferred embodiments of the present universal passive protector 20 for an IV catheter comprise an over-the-needle catheter 22 including a hub 24 attached at a proximal end 26 of the catheter 22. A proximal end 28 (FIG. 1D) of the hub 24 is captured between two retractable arms 30 comprising a hub trap 32. The hub trap 32 is in turn connected at a proximal end to a distal end of a sheath 34. In the embodiment of FIG. 1A, the sheath 34 has a substantially square cross-section, while in the embodiments of FIGS. 1B and 1C, the sheath 34 has a substantially round cross-section. One of skill in the art will appreciate that the sheath 34 may have a variety of alternative cross-sectional shapes without departing from the spirit of the protector 20.

Figure 3:
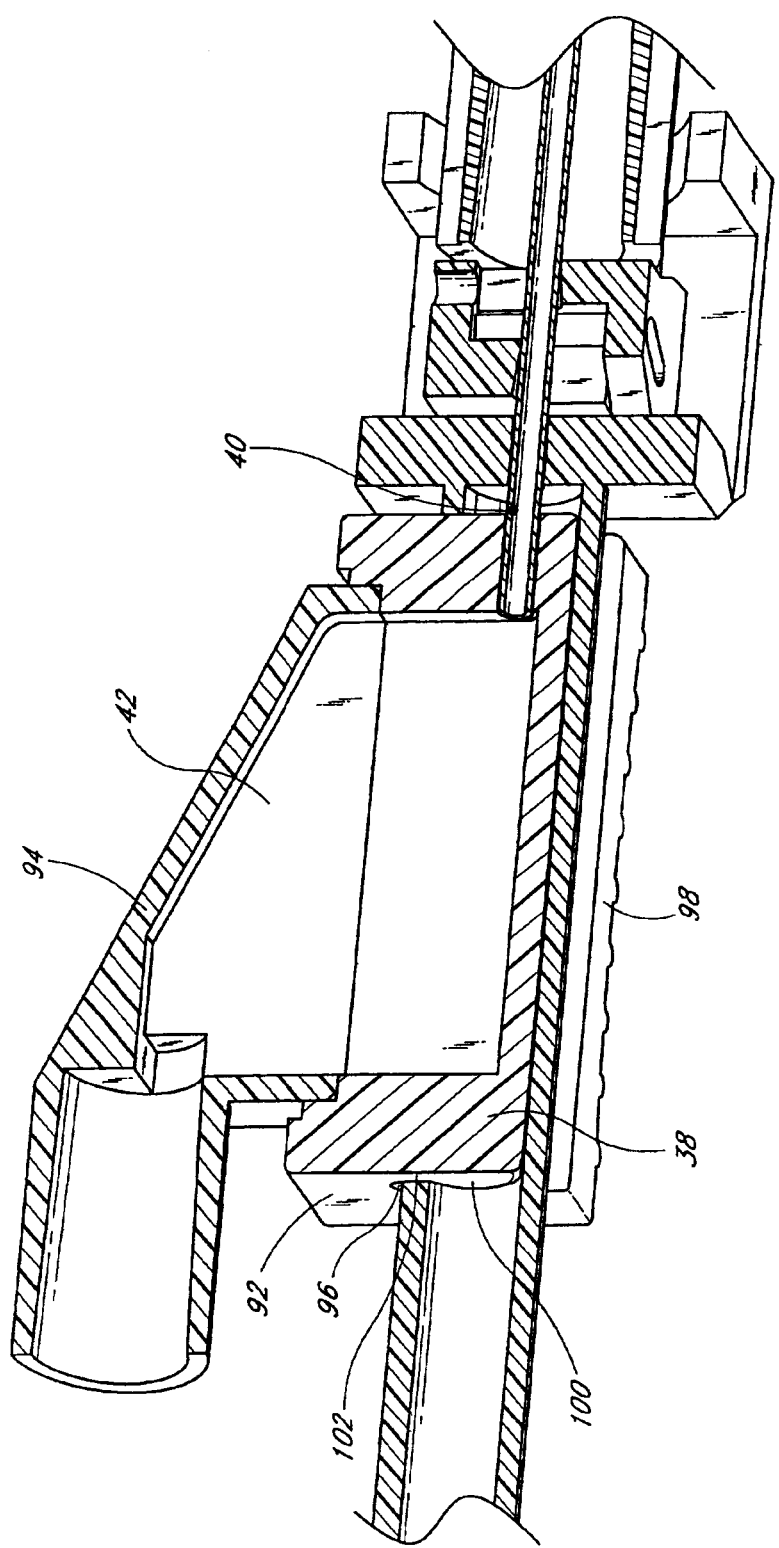
FIG. 3 is a side perspective section view of the slide/hub trap/hub portion of the universal passive protector for an IV catheter of FIG. 1B.

The sheath 34 includes a longitudinal slit 36 extending from a distal end to a proximal end. A slider 38 is disposed about the outside of the sheath 34. The slider 38 is connected through the slit 36 to a proximal end of a needle 40 (FIG. 3). In preferred embodiments, the slider 38 includes an attached flashback chamber 42, the function of which is described below.

In FIGS. 1A, 1B and 1C, the slider 38 is positioned at a distal end of the sheath 34. In this configuration, the needle 40 extends through the hub trap 32, through the hub 24, and through the catheter 22. A sharp distal tip 44 of the needle 40 protrudes from a distal end of the catheter 22. First and second arms 30 of the hub trap 32 abut one another, defining a closed position in which the hub 24 is held securely between the arms 30. The arms 30 are biased toward an open position. The needle 40, however, retains the arms 30 in the closed position in a manner described below.

Figure 1D:
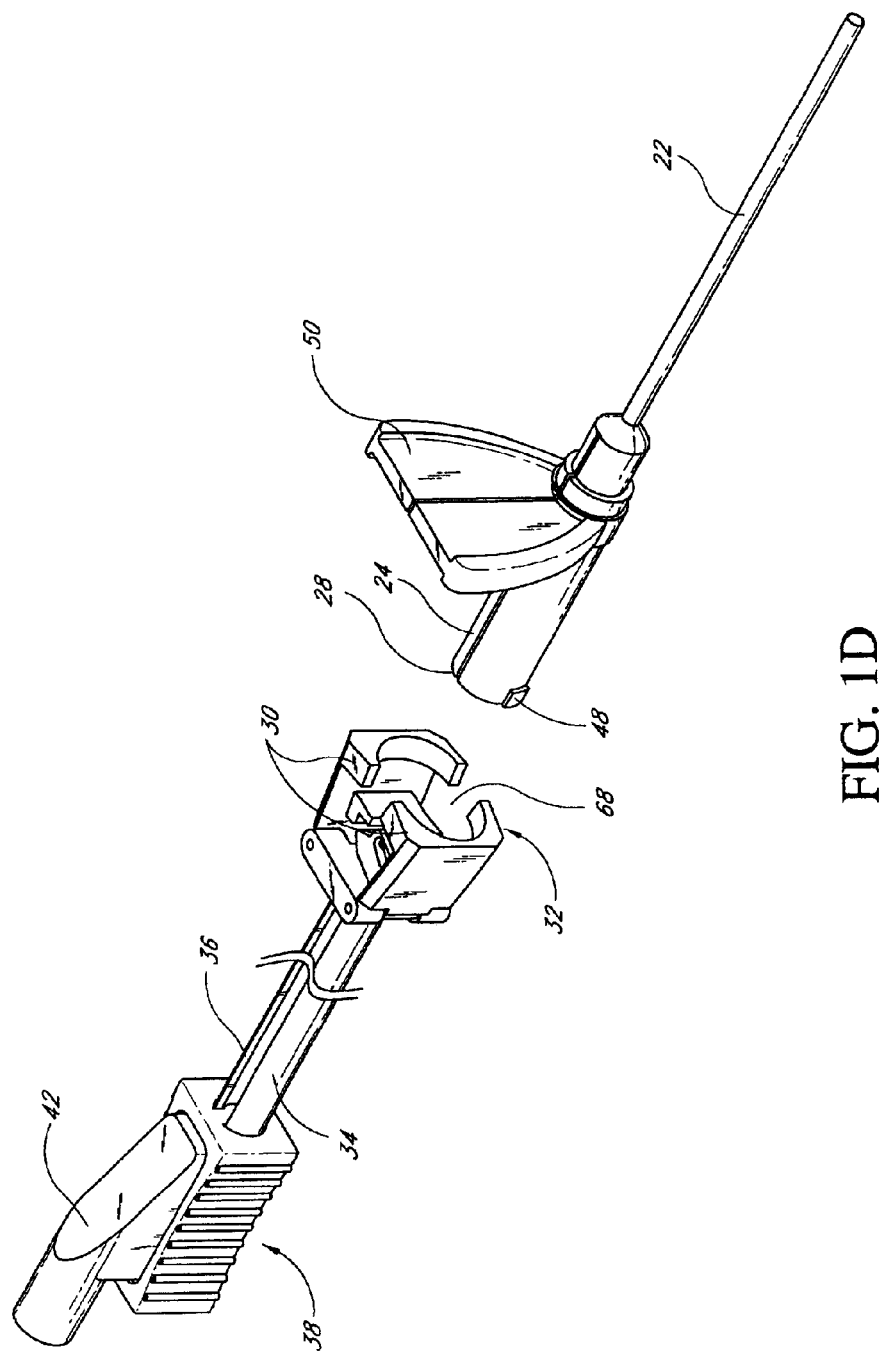
FIG. 1D is a perspective view of the universal passive protector for an IV catheter of FIG. 1C, illustrating the arms in the open position.

The slider 38 is movable along the sheath 34 to a proximal position, shown in FIG. 1D. A stop 46 at the proximal end of the sheath 34 prevents the slider 38 from detaching from the sheath 34. In the embodiment of FIG. 1A, the stop 46 comprises a substantially square boss on each of oppositely facing outer surfaces of the sheath 34. In the embodiments of FIGS. 1B and 1C, the stop 46 comprises a ring disposed within an interior of the sheath 34. One of skill in the art will appreciate that a variety of alternative stops may be equally effective.

In the configuration illustrated in FIG. 1D, the needle 40, which translates with the slider 38, is disposed within the sheath 34. The arms 30 are pivoted outward, defining an open position of the hub trap 32. In the open position the arms 30 prevent the reemergence of the sharp needle tip 44 from the sheath 34 in a manner described below. Healthcare personnel are thus protected from accidental needle sticks that an exposed needle 40 could cause after the catheter 22 is inserted. Because the arms 30 do not abut one another in the open position, the hub 24 is released from the hub trap 32, and is capable of receiving connecting devices, such as an IV.

The hub 24 comprises a generally cylindrical tube having a first radial protrusion 48 (FIG. 1D) and a second, opposite, radial protrusion (not shown) at a proximal end 28. The protrusions 48 enable the hub trap 32 to securely hold the hub 24, as explained below. The protrusions 48 also enable a luer lock to be securely fastened to the hub 24 after the catheter 22 is emplaced within a patient's vein.

In the pictured embodiment, the hub 24 includes a medial fin 50 defining a plane perpendicular to a longitudinal axis of the hub 24. The fin 50 provides a convenient surface for a healthcare technician to grasp when inserting the catheter 22, as explained below. However, one of skill in the art will understand that the fin 50 is not vital to achieving the advantages of the protector 20, and embodiments not including the fin 50 do not depart from the spirit of the protector 20.

In the embodiment of FIG. 1A, an upwardly projecting tab 51 is provided on the hub trap 32. The tab 51 provides a push-off point against which a healthcare technician places his or her index finger when operating the protector, as further explained below. One of skill in the art will understand that the tab 51 may also be provided on either of the embodiments pictured in FIG. 1B or 1C. One of skill in the art will also understand that the tab 51 is not vital to achieving the advantages of the protector 20, and embodiments not including the tab 51 do not depart from the spirit of the protector 20.

A typical catheter 22, comprising a flexible tube with a blunt distal tip, is attached to the distal end of the hub 24. A central lumen 52 (FIG. 5A) passes through the hub 24 and the catheter 22. After insertion, the distal tip of the catheter 22 is disposed within a patient's vein, thereby providing a path for intravenous injection or aspiration of the patient. The first and second radial protrusions 48 on the proximal end of the hub 24 enable injection/aspiration devices to be attached to the hub 24 via a threaded luer lock.

Figure 4A:
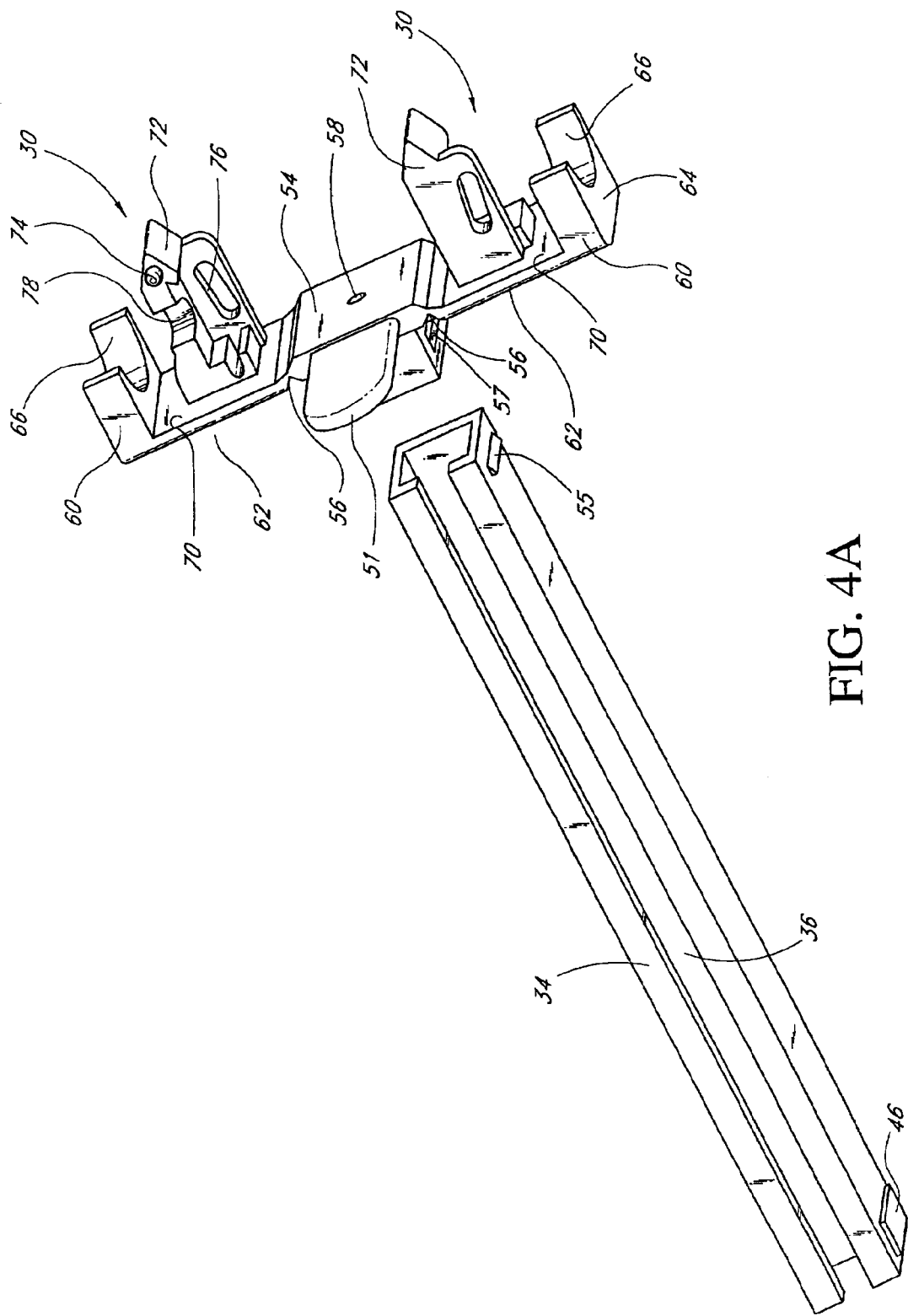
FIG. 4A is a perspective view of the sheath/hub trap of the universal passive protector for an IV catheter of FIG. 1A.

One preferred embodiment of the arms 30 is illustrated in FIG. 4A. Preferably the arms 30 are molded as a unitary piece including a base plate 54. The arms are thus simple and cheap to manufacture, because no complicated assembly is involved. The arms may, for example, be manufactured from a thermoplastic using an injection molding technique. A narrow, flexible portion 56 connects each arm 30 to the base plate 54, such that the arms 30 are pivotable about the base plate 54.

The base plate 54 is substantially flat and rectangular, defining a plane perpendicular to a longitudinal axis of the protector 20. The sheath 34 is attached to a proximal face of the base plate 54. The sheath 34 is preferably molded as a separate piece, and attached to the arms 30 via a snap fit secured with interlocking tabs 55 and slots 57. In lieu of interlocking tabs and slots, the arms 30 may instead be secured to the sheath 34 via, for example, a friction fit or an adhesive.

Figure 4B:
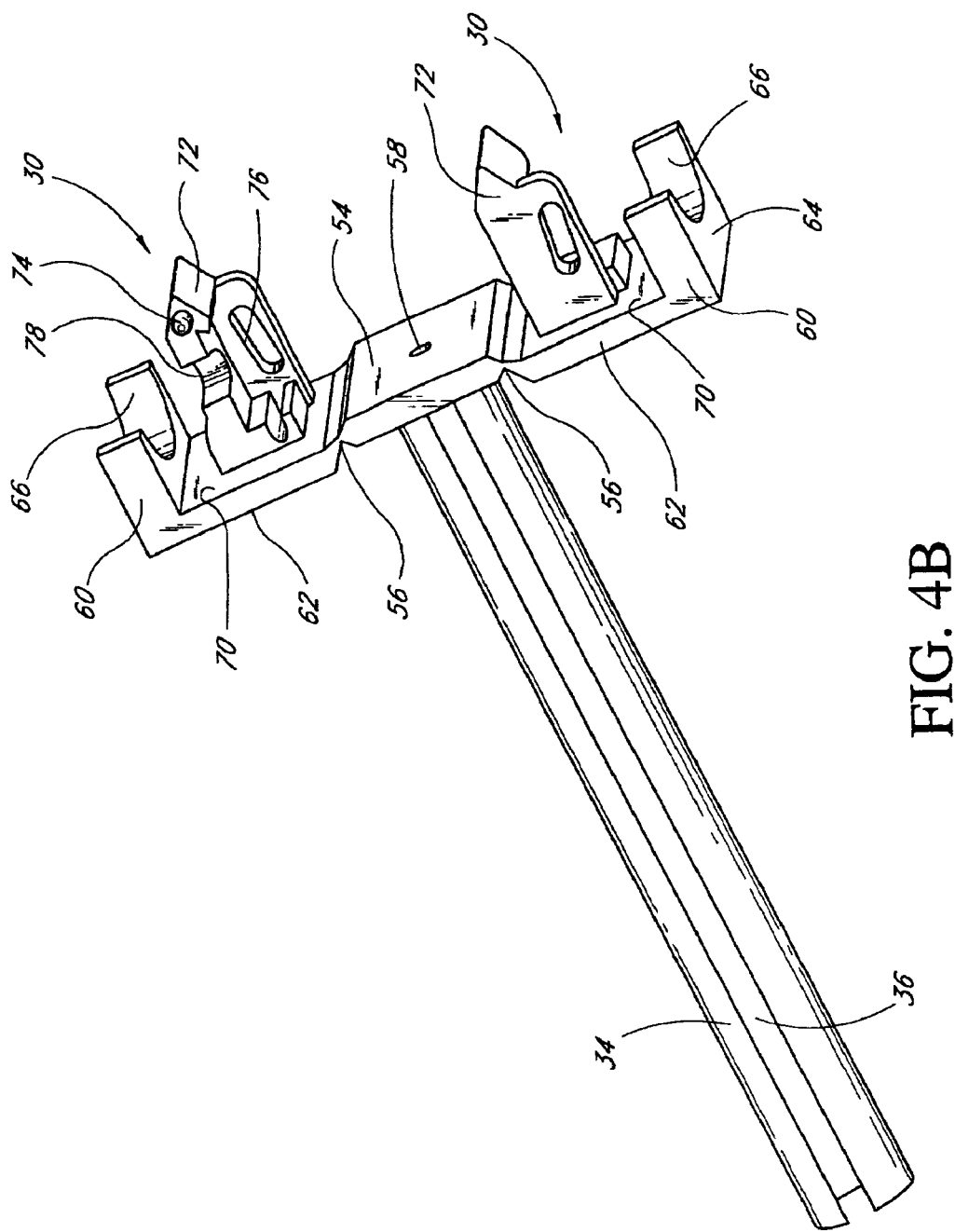
FIG. 4B is a perspective view of the sheath/hub trap of the universal passive protector for an IV catheter of FIG. 1B.

Another preferred embodiment of the arms 30 is depicted in FIG. 4B. In this embodiment, the sheath 34 is preferably molded as a unitary piece together with the base plate 54 and arms 30.

A through-hole 58 in the center of the base plate 54 is in fluid communication with the sheath 34. A periphery of each arm 30 resembles an L in plan aspect, comprising a base portion 60 and a leg portion 62. Each of the base and leg portions comprise a substantially flat plate. In their natural configuration, as they appear immediately after manufacture, the leg portions 62 of the arms 30 preferably define a plane that is parallel to the plane defined by the base plate 54, as pictured in FIGS. 4A and 4B. Because the arms 30 are connected to the base plate 54 via narrow, deformable portions 56, or hinges, the arms 30 are pivotable toward the distal end of the protector 20. The shape memory of the material, however, biases the arms 30 back toward their natural positions.

The base portion 60 of each L comprises a distal face 64 including a semicircular cut-out 66. When the arms 30 are in the closed position, the plane defined by the leg portion 62 of each arm 30 is substantially parallel to the longitudinal axis of the protector 20, and the semi-circular cut-outs 66 define a circular opening 68 (visible only in FIG. 1D, wherein the arms are not actually in the closed position). Preferably, a diameter of the opening 68 is substantially the same as a diameter of the proximal end 28 of the hub 24. The radial protrusions 48 on the proximal end 28 of the hub 24, however, preferably extend beyond the diameter of the opening 68. With the hub 24 disposed within the opening 68 such that the radial protrusions 48 are captured on the proximal side of the opening 68, the radial protrusions 48 prevent the hub 24 from exiting the opening 68 and releasing from the arms 30.

Figure 2A:
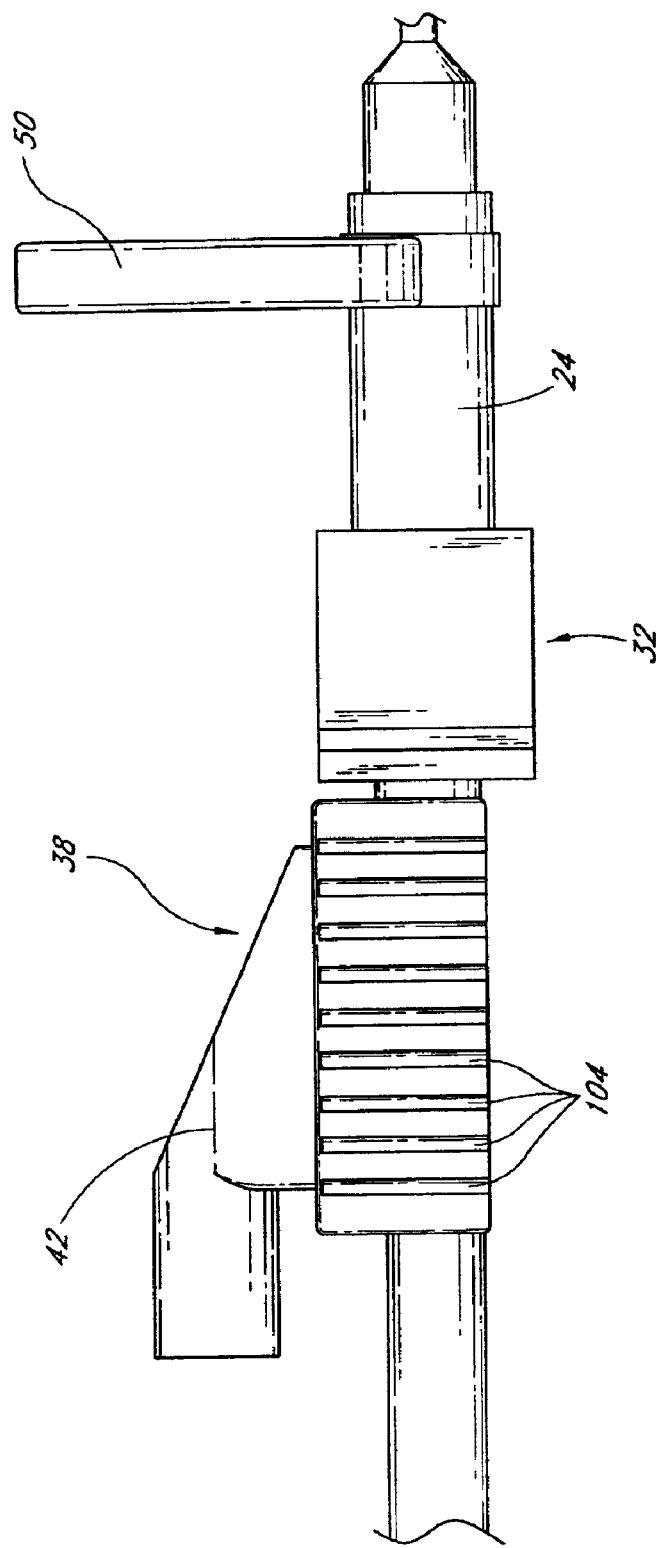
FIG. 2A is a front elevation view of the slide/hub trap/hub portion of the universal passive protector for an IV catheter of FIG. 1B.
Figure 2B:
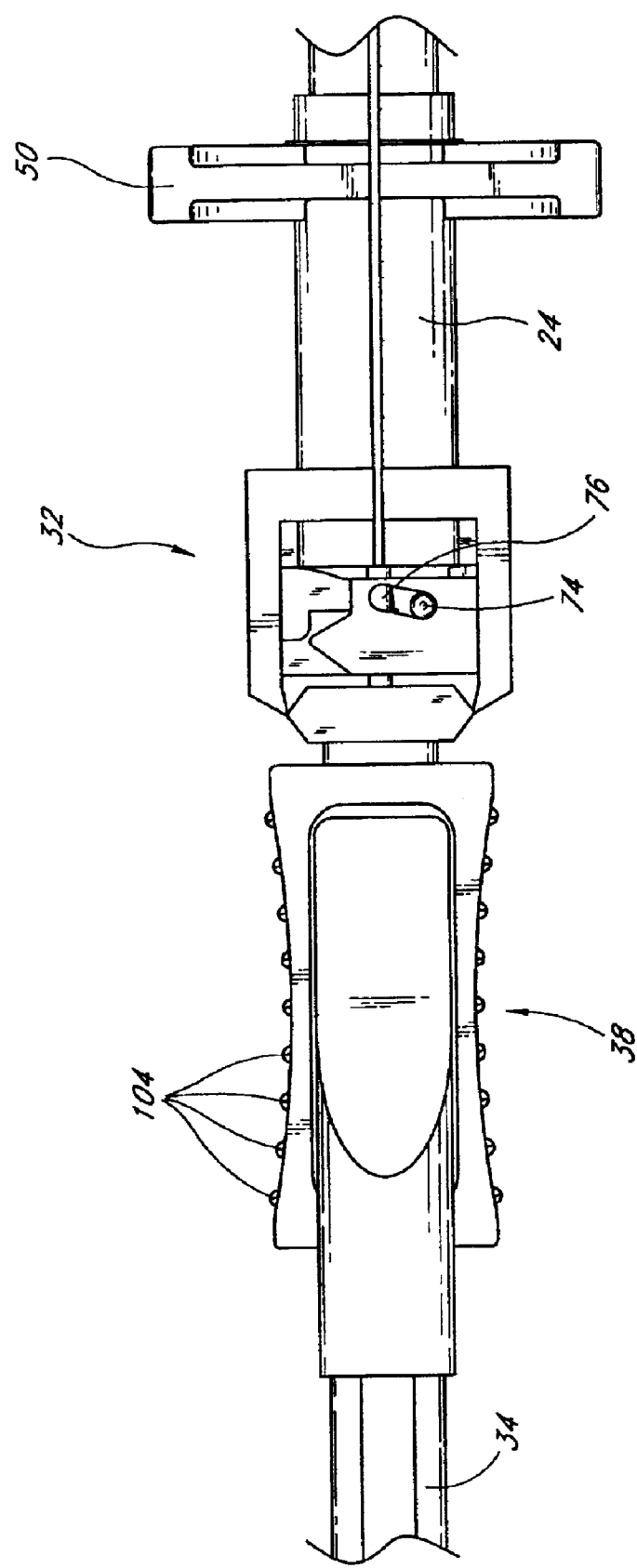
FIG. 2B is a top plan view of the slide/hub trap/hub portion of the universal passive protector for an IV catheter of FIG. 1B.
Figure 2C:
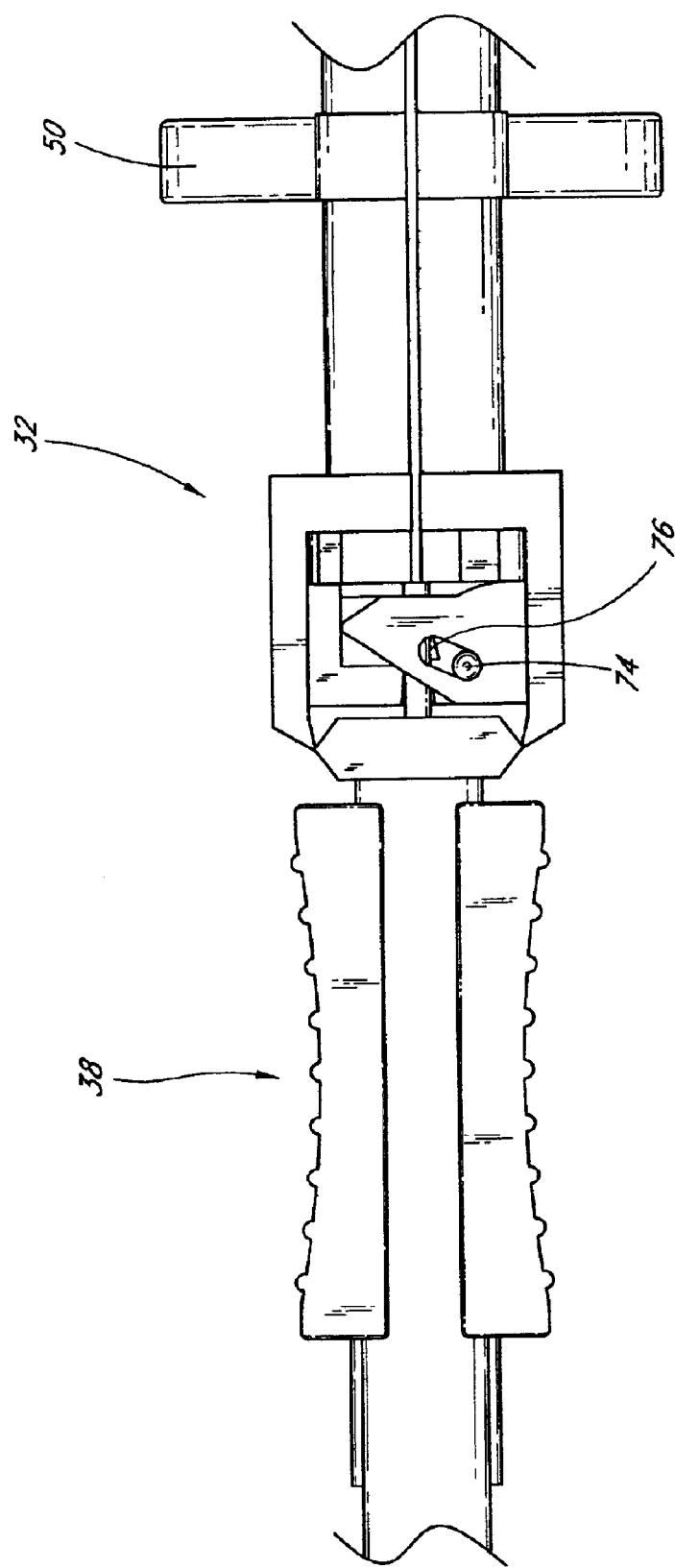
FIG. 2C is a bottom plan view of the slide/hub trap/hub portion of the universal passive protector for an IV catheter of FIG. 1B.

An inside face 70 of each leg portion 62 of each arm 30 includes a locking structure. The locking structure comprises first and second branches 72, one branch 72 being disposed on each arm 30. Each branch 72 includes a boss 74 on a first surface, and a channel 76 in a second, parallel surface. Because each branch 72 is an inverted mirror image of the other, the boss 74 on each branch 72 interconnects with the channel 76 on the opposite branch when the arms 30 are pivoted from their natural configuration toward the closed position (FIGS. 2B and 2C). With the branches 72 interconnected as in FIGS. 1C, 1D and 2B, the movement of the bosses 74 within the channels 76 guides the relative motion of the arms 30. Because the bosses 74 and channels 76 interlock in an over-under fashion, each arm 30 prevents the other from rotating about any axis other than the hinges 56.

Figure 5A:
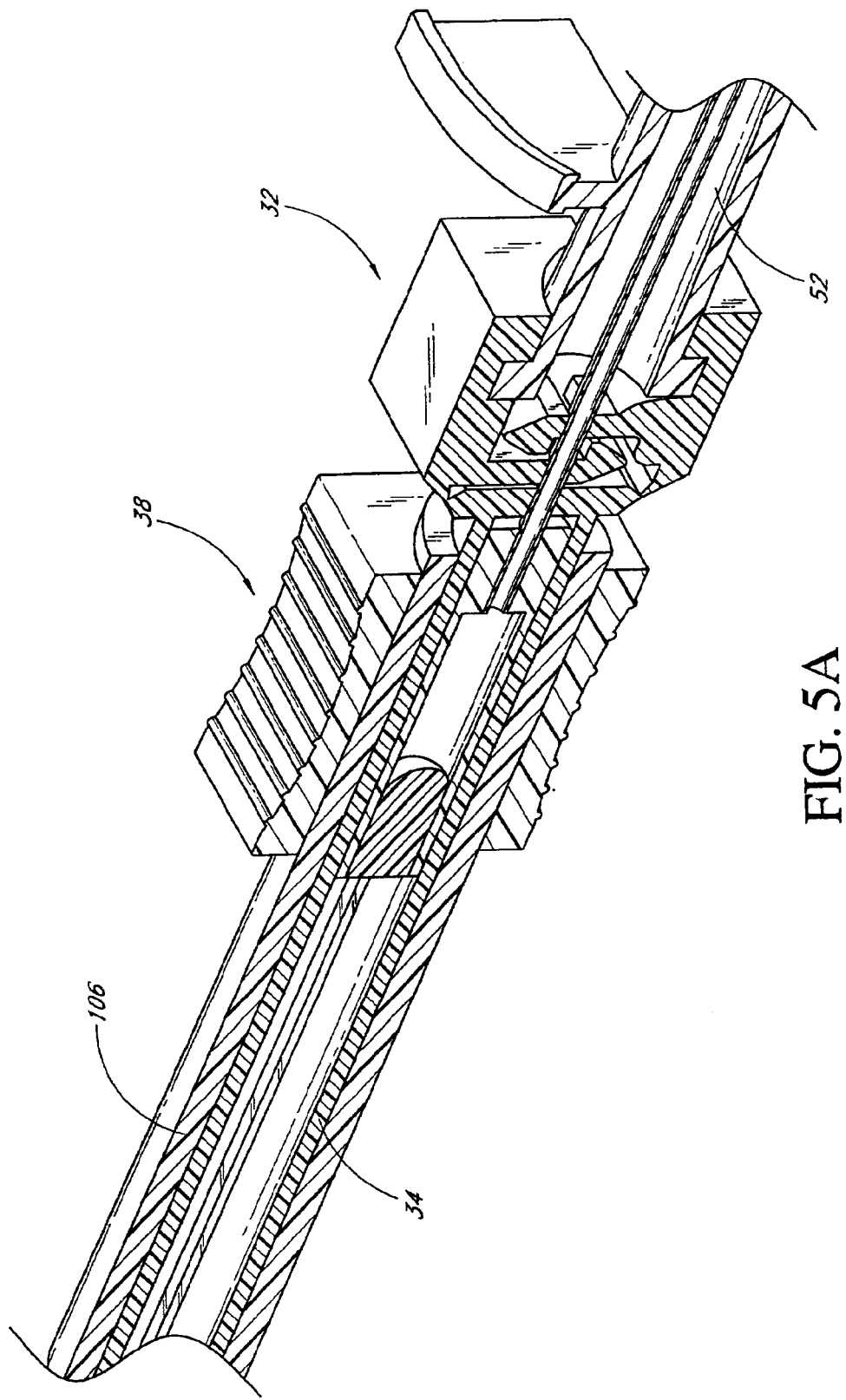
FIG. 5A is a bottom perspective section view of the slide/hub trap/hub portion of an alternative embodiment of the universal passive protector for an IV catheter including a telescoping sheath, illustrating the arms in the closed position.
Figure 5B:
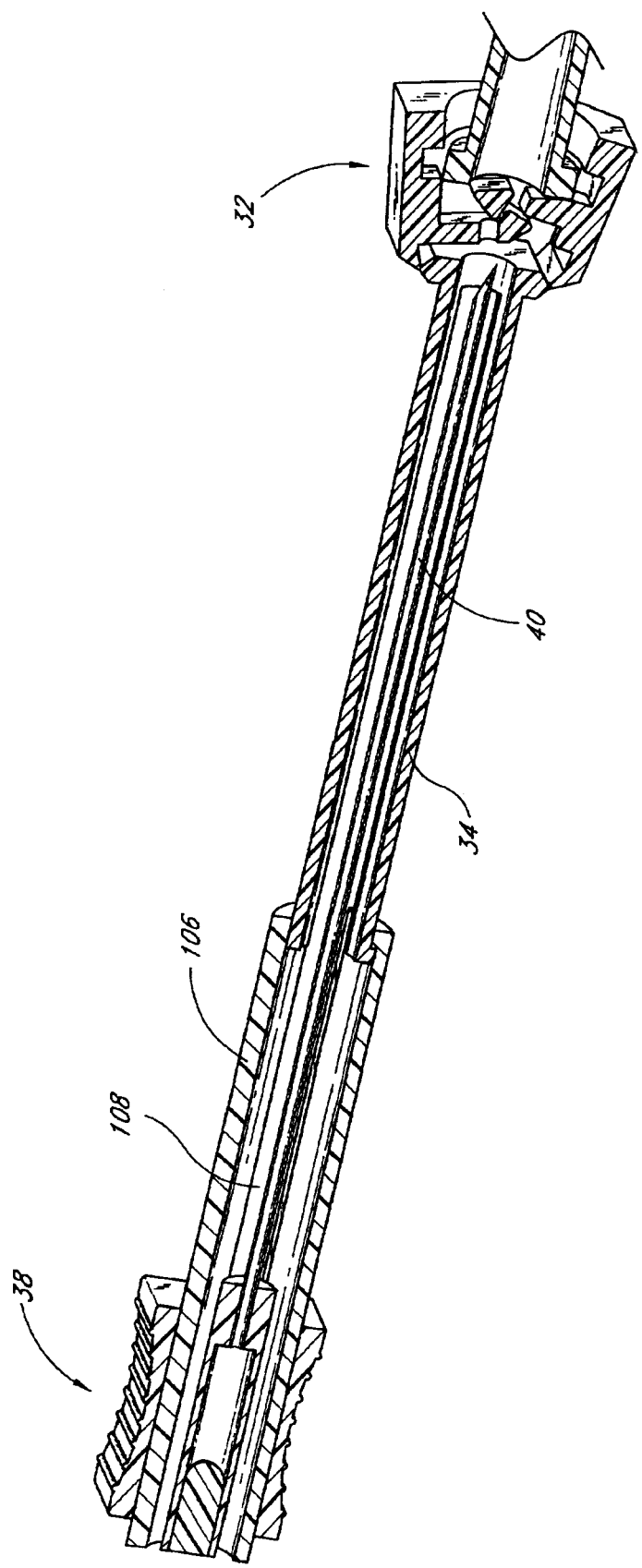
FIG. 5B is a bottom perspective section view of the slide/hub trap/hub portion of the universal passive protector for an IV catheter of FIG. 5A, illustrating the arms in the open position.

Each branch 72 includes a semi-circular gap 78 (FIG. 4A). Each gap 78 is oriented such that when the arms 30 are in the closed position, the gaps 78 line up to form a substantially circular passageway that is coaxial with the central through-hole 58 in the base plate 54. A path is thus created through which a central portion of the needle 40 is disposed (FIG. 5A). The spring force biasing each arm 30 toward its resting position forces a sidewall of each gap 78 to contact the needle 40. Removal of the needle 40 from between the gaps causes the arms 30 to spring away from one another (FIG. 5B).

Figure 6:
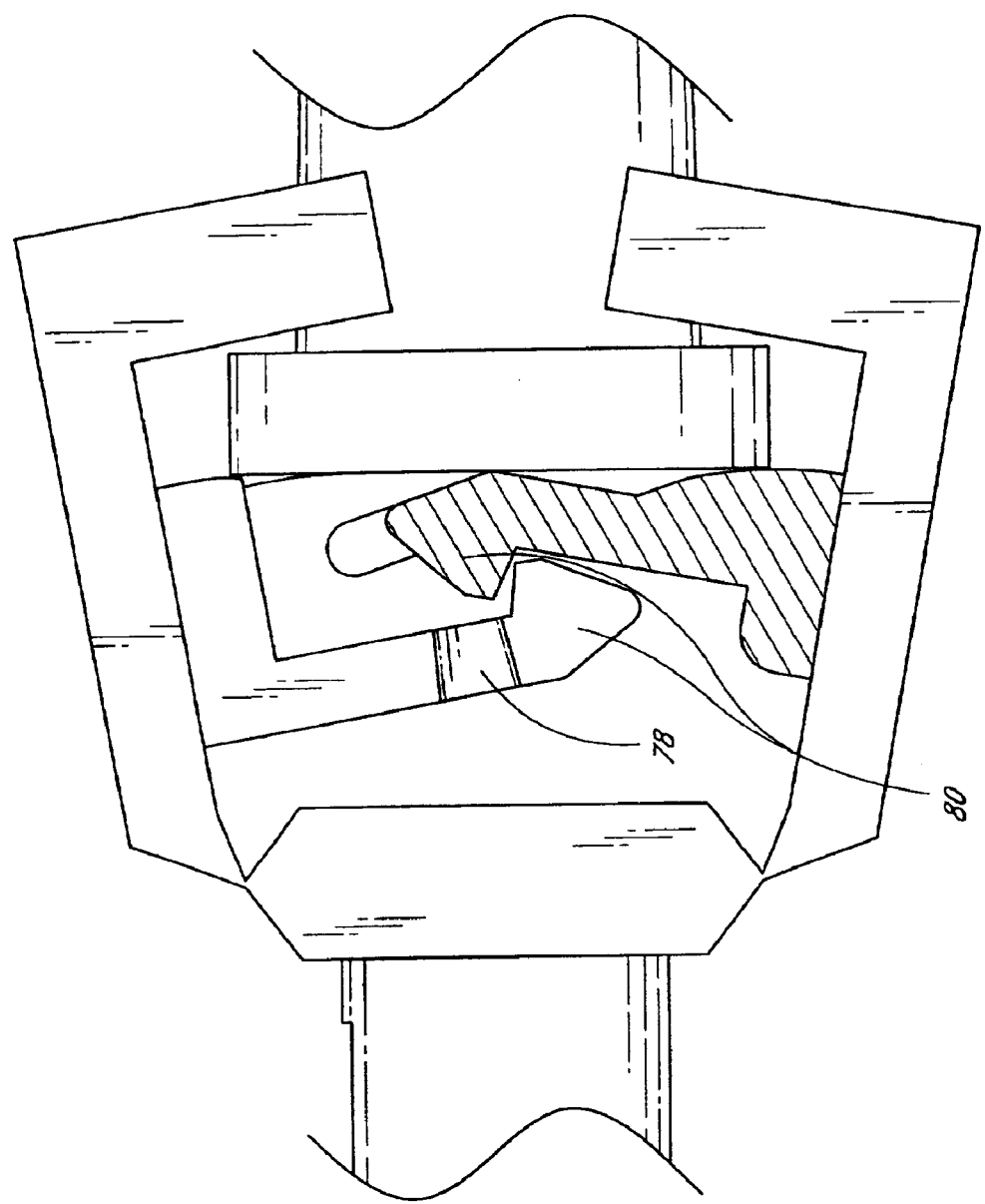
FIG. 6 is a bottom plan view of the arms of the universal passive protector for an IV catheter of FIG. 1B, illustrating the arms in the open position.
Figure 7:
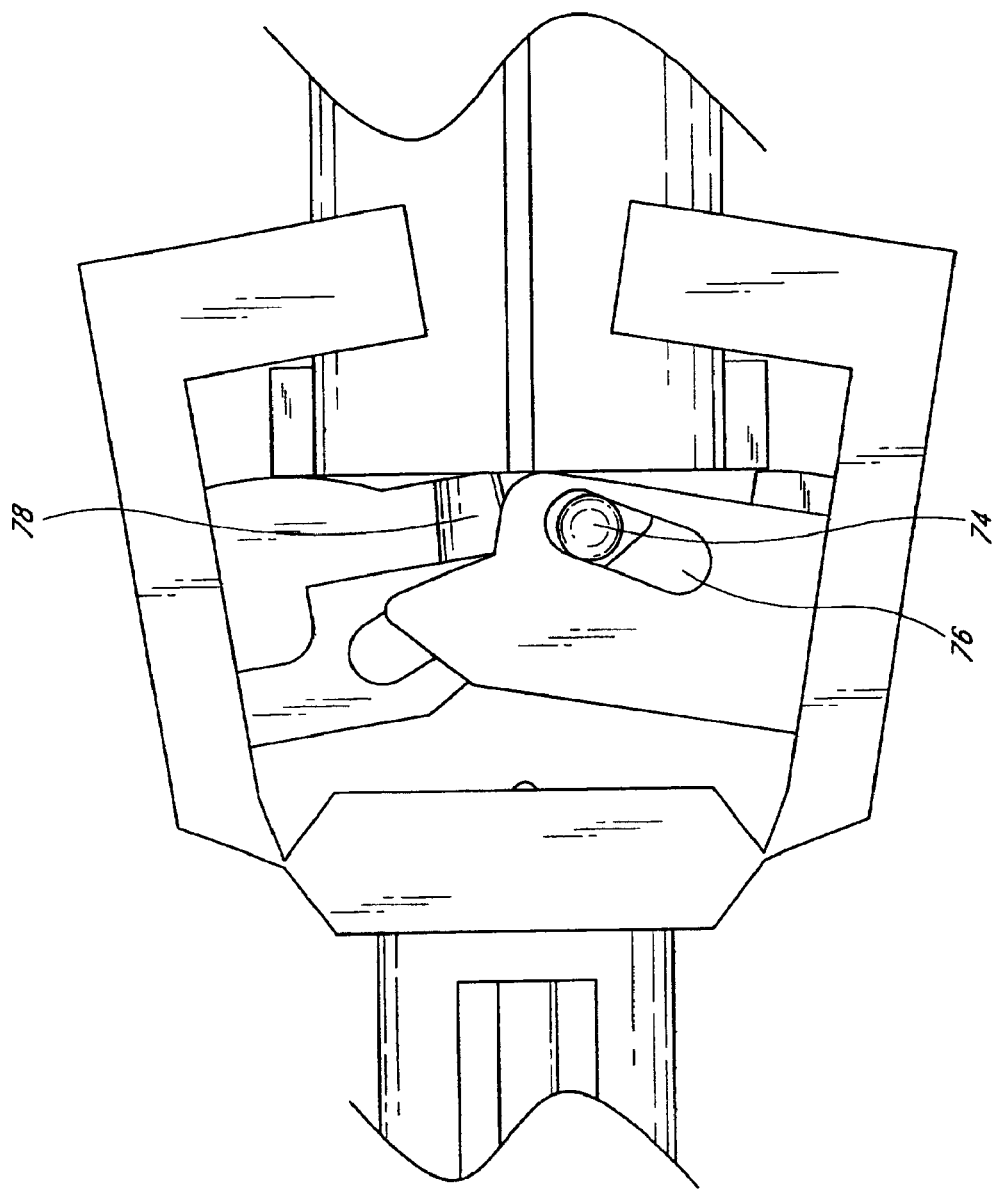
FIG. 7 is a top plan view of the arms of the universal passive protector for an IV catheter of FIG. 1B, illustrating the arms in the open position.

As best seen in FIG. 6, each branch also includes an interlocking finger 80. In plan aspect, each finger 80 comprises a ledge protruding from a proximal face of the branch 72. When the branches 72 are interlocked, such that each boss 74 is disposed within its corresponding slot 76, the spring forces tending to return the arms 30 to their resting positions cause the fingers 80 to contact each other, as in FIG. 6. The fingers 80 thus prevent the arms 30 from springing back to their natural positions. This configuration, with the fingers 80 in contact, defines the open position of the hub trap 32, as seen in FIG. 1D.

In the open position, the circular opening 68 is widened as compared to the closed position. The hub 24 is thus removable from the arms 30, because a width of the circular opening 68 (which is no longer actually circular) is wider than a width of the portion of the proximal end of the hub 24 including the radial protrusions 48. Further, the interlocked fingers 80 are positioned directly in front of the central through-hole 58 in the base plate 54. The fingers 80 thus prevent the needle 40 from emerging from the sheath 34, and protect against accidental needle sticks.

Figure 4C:
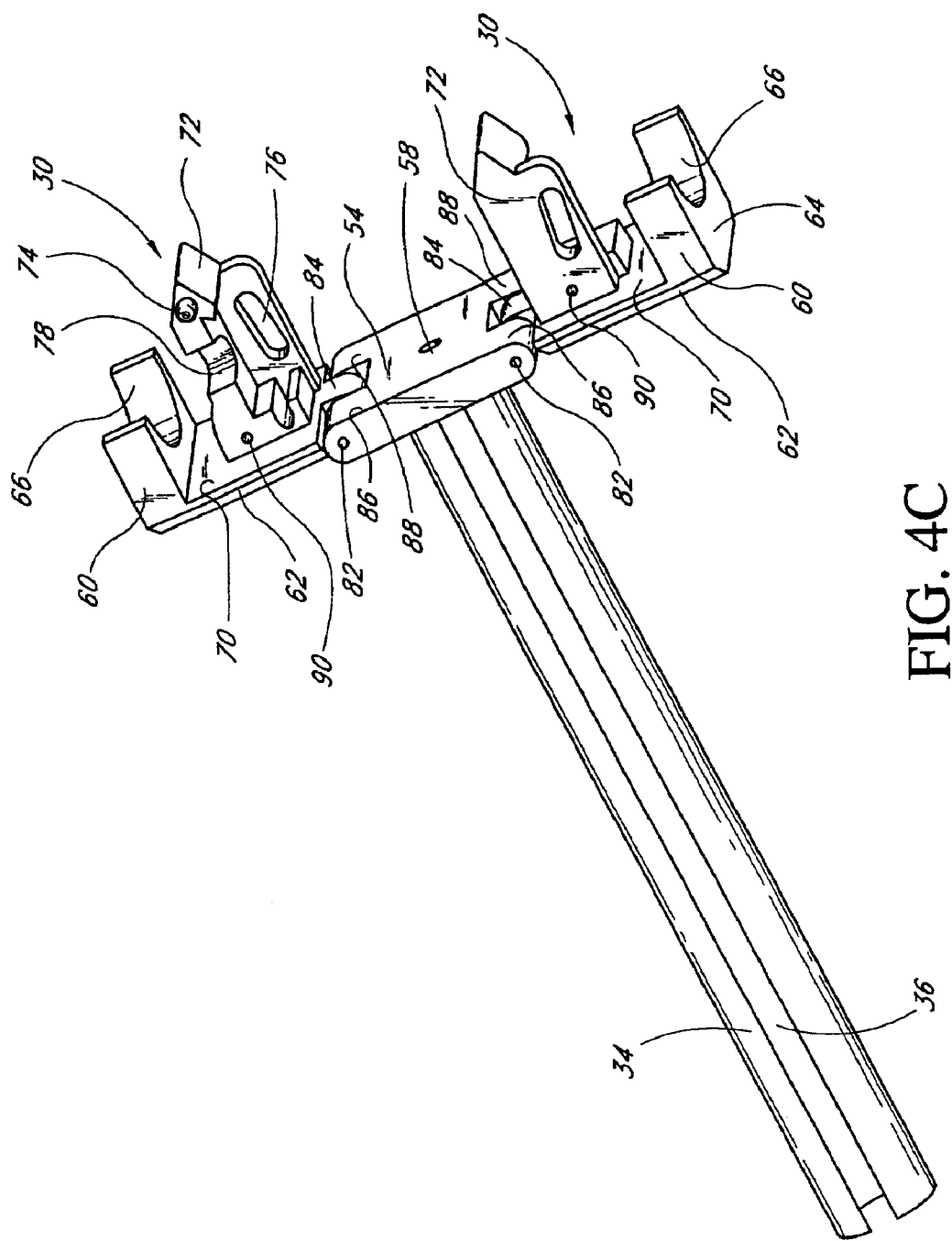
FIG. 4C is a perspective view of the sheath/hub trap of the universal passive protector for an IV catheter of FIG. 1C.

Another preferred embodiment of the arms 30 is depicted in FIG. 4C. In this embodiment, the arms 30 are not formed as a unitary member with the base plate 54. Rather, each arm 30 is hingedly connected to the base plate 54 via a hinge pin 82. The base portion 62 of each arm 30 includes a first hinge member 84 that is shaped substantially as a half-oval in plan aspect. The first hinge member 84 includes a through-hole (not shown) defining a hinge axis. The hinge axis is parallel to the planes of the leg portion 62 and base portion 60. The first hinge member 84 is captured between second and third hinge members 86, 88 that extend from the base plate 54. The second and third hinge members 86, 88 include coaxial through-holes (not shown) that are also coaxial with the first hinge member through-hole. A substantially cylindrical hinge pin 82 extends through the through-holes in the first, second and third hinge members 84, 86, 88 to pivotably secure each arm 30 to the base plate 54. One of skill in the art will appreciate that the illustrated hinge configuration is merely exemplary. Each arm 30 may include more hinge members, and the base plate 54 may include more or less hinge members.

The arms 30 of this embodiment include locking structure substantially identical to that of the arms 30 illustrated in FIGS. 4A and 4B. The arms 30 of FIG. 4C are not naturally biased toward the open position, however. Thus a spring (not shown) biases the arms 30 toward the open position. In the pictured embodiment, each branch includes a vertical through-hole 90. The spring comprises a thin wire bent in two locations. Each end portion of the spring is disposed within one of the through-holes 90. Stored energy in the spring biases the arms 30 toward the open position.

In FIGS. 1A, 1B and 1C, a hypodermic needle 40 is disposed within the catheter 22. The needle 40 comprises a cylindrical tube with a central lumen 52. A sharp distal tip 44 enables the needle 40 to puncture a patient's skin in order to establish fluid communication between the patient's vein and the catheter 22. A proximal end of the needle 40 is connected to the slider 38 (FIG. 3). The slider 38 depicted in FIGS. 1B and 1C comprises a generally rectangular box-shaped portion 92 with a generally wedge-shaped portion 94 attached to a top of the box, and a longitudinal slot 96 in an underside of the box 92. The slot 96 may be open on a bottom surface 98 of the box 92.

In the embodiment of FIGS. 1B and 1C, a solid cylindrical portion 100 is suspended from an upper wall of the slot 96 by a short rectangular neck 102. In the embodiment of FIG. 1A, An axis of the cylinder 100 preferably coincides with an axis of the sheath 34. The cylindrical portion 100 is disposed within the sheath 34, with the rectangular neck 102 captured between opposite sides of the slit 36. Preferably, a diameter of the cylinder 100 is greater than a width of the slit 36. The cylinder 100 thus helps to stabilize the slider 38 and prevent it from disengaging the sheath 34. The slider 38 may include textured side portions 104 (FIG. 2A) to enable a medical technician to better grip the slider 38. In the pictured embodiments, the textured portions 104 comprise raised vertical bars.

The slider 38 depicted in FIG. 1A is shaped similarly to the slider 38 depicted in FIGS. 1B and 1C, with a few exceptions that adapt the slider 38 to fit about the sheath 34 having a substantially square cross-section. Also, side walls of the slider 38 preferably flare outwardly from a distal end of the slider 38 toward a proximal end of the slider 38. The flared portions enhance the ability of a medical technician to grip the slider 38 when operating the protector 20. Operation of the protector is outlined below.

As shown in FIG. 3, the slider 38 includes a hollow interior chamber, or "flashback" chamber 42. The flashback chamber 42 is in fluid communication with the lumen 52 through the cylinder 100. Thus, when the needle 40 punctures the patient's vein, blood flows from the patient into the flashback chamber 42. At least one wall of the flashback chamber 42 preferably includes a transparent portion. The interior of the flashback chamber 42 is thus visible to a medical technician, who can determine, based on the presence or absence of blood within the flashback chamber 42, whether the needle 40 has been properly inserted into the patient's vein.

FIGS. 5A and 5B illustrate another preferred embodiment of the protector 20 including a telescoping sheath 106. The telescoping sheath 106 is substantially a hollow cylinder including a longitudinal slit 108 in an upper surface. The telescoping sheath 106 is slidably disposed about the sheath 34 such that the longitudinal slit 108 aligns with the longitudinal slit 36. The slider 38 is slidably disposed about the telescoping sheath 106 such that the rectangular neck 102 extends through both the longitudinal slit 108 and the longitudinal slit 36. One of skill in the art will appreciate that the sheath 34 including a substantially square cross-section may also be of a telescoping construction.

Operation

To insert a catheter 22 into a patient's vein using the protector 20, a medical technician grasps the protector 20 with two hands in whatever way is most comfortable. The technician punctures the patient's skin with the sharp distal tip 44 of the needle 40 and guides the needle 40 into a vein. When the needle 40 has penetrated a vein, the flashback chamber 42 fills with blood. The technician inserts the needle 40 into the vein deeply enough so that the distal end of the catheter 22 traverses a wall of the vein.

When the catheter 22 has been safely inserted into the vein, the technician grasps the fin 50 with one hand, and the slider 38 with the other hand. Holding the fin 50 still so as to steady the catheter 22, the technician draws the slider 38 back, toward the proximal end of the sheath 34. If the protector includes a tab 51, such as the embodiment of FIG. 1A, the technician uses his or her index finger, on the same hand that grasps the slider 38, to push against the tab 51. The needle 40 is thus drawn into the sheath 34, which acts as a barrier between the medical technician and any bodily fluids present on the needle 40. With the embodiment including the telescoping sheath 106, the slider 38, the telescoping sheath 106, and the sheath 34 all slide relative to one another. When the needle 40 is fully encased within the sheaths 34, 106, the slider 38 may be disposed about the proximal portion of the telescoping sheath 106, and the distal portion of the telescoping sheath 106 may be disposed about the proximal portion of the sheath 34, as in FIG. 5B. Advantageously, the embodiment including the telescoping sheath 106 is capable of encasing long needles, but does not greatly increase the overall length of the protector 20 in the unused configuration.

When the distal needle tip 44 passes to the proximal side of the gaps 78 (FIG. 5B), the arms 30 are no longer restrained by the needle 40 and thus spring into the open position. The catheter 22 is thus released from the arms 30, and is ready to receive an injection or aspiration device. The needle 40 is safely stowed within the sheath 34. The interlocking fingers 80 block the path of the needle 40, preventing it from reemerging from the sheath 34. In contrast to prior art devices that rely on a frictional engagement between the needle and a locking cam in order to keep the sharp needle tip safely stowed, the protector 20 provides a sheath 34 that is closed at both ends. In order for the needle distal tip 44 to exit the sheath 34, the arms 30 must be pinched at the same time the slider 38 is moved toward the distal end of the sheath 34. This combination of events is unlikely to occur accidentally. The technician is thus well protected against an accidental needle stick.

The protector 20 provides a virtually danger-free method of inserting a catheter 22. Once the distal tip of the catheter 22 penetrates the patient's vein, the sharp needle tip 44 is never again exposed. As the operator draws the slider 38 back, the needle 40 is disposed first within the catheter 22, then within the hub 24, and finally within the hub trap 32. The hub trap 32 does not release the hub 24 until the needle tip 44 is safely stowed within the hub trap 32. Once the needle 40 is safely stowed, the interlocking fingers 80 prevent its reemergence from the safety of the hub trap 32.

The easy gliding motion of the slider 38 also contributes to a virtually needle stick-free protector 20. Because the slider 38 is so easy to manipulate, the operator can withdraw the needle 40 without any uncertain, jerking movements that could cause a needle stick, or that could cause the catheter 22 to withdraw from the vein. The protector 20 thus provides a means of emplacing a catheter 22 that is not only safe, but also efficient. An operator seldom needs to discard the catheter 22 and start again.

SCOPE OF THE INVENTION

The above presents a description of the best mode contemplated for the present universal passive protector for an IV catheter, and of the manner and process of making and using it, in such full, clear, concise, and exact terms as to enable any person skilled in the art to which it pertains to make and use this universal passive protector for an IV catheter. This universal passive protector for an IV catheter is, however, susceptible to modifications and alternate constructions from that discussed above which are fully equivalent. Consequently, it is not the intention to limit this universal passive protector for an IV catheter to the particular embodiments disclosed. On the contrary, the intention is to cover all modifications and alternate constructions coming within the spirit and scope of the universal passive protector for an IV catheter as generally expressed by the following claims, which particularly point out and distinctly claim the subject matter of the universal passive protector for an IV catheter.

What is claimed is:

1. A universal passive protector for an IV catheter, comprising:
   a hypodermic needle;
   an over-the-needle catheter, including a hub, disposed about the needle;
   a hub trap comprising first and second arms and a locking structure;
   an elongate sheath; and
   a slider connected to a proximal end of the needle, the slider being movable along the sheath from a distal position to a proximal position; wherein
   when the slider is in the distal position, the needle extends through and cooperates with the locking structure of the hub trap so as to retain the first and second arms in a closed position wherein the hub is trapped between the first and second arms; and
   when the slider is in the proximal position, a distal tip of the needle is proximal of the locking structure and the first and second arms are in an open position wherein the hub is released from the hub trap.

2. The protector of claim 1, wherein the hub is released only when the slider is in the proximal position, and remains trapped within the hub trap when the slider is in the distal position or in any position intermediate the distal position and the proximal position.

3. The protector of claim 1, wherein when the slider is in the distal position or in any position intermediate the distal position and the proximal position, the needle contacts the arms and provides a force counteracting a spring force biasing the arms toward the open position.

4. The protector of claim 1, wherein when the arms are in the open position, interlocking fingers of the first and second arms block the needle and prevent it from reemerging from the sheath.

5. The protector of claim 1, wherein a stop is positioned at a proximal end of the sheath and prevents the slider from disengaging the sheath via the proximal end.

6. The protector of claim 1, wherein the arms are pivotable about an axis substantially perpendicular to a longitudinal axis of the protector.

7. The protector of claim 1, wherein the slider comprises a hollow interior chamber in fluid communication with a central lumen of the needle.

8. The protector of claim 7, wherein a portion of the slider is transparent and allows viewing of the interior chamber.

9. The protector of claim 1, wherein the sheath comprises a first substantially cylindrical member.

10. The protector of claim 9, wherein the sheath further comprises a second substantially cylindrical member slidably disposed about the first member, such that the first and second members are telescoping.

11. The protector of claim 1, wherein the hub further comprises a substantially flat fin defining a plane substantially perpendicular to a longitudinal axis of the protector.

12. A universal passive protector for an IV catheter, comprising:
    a hypodermic needle;
    an over-the-needle catheter, including a hub, disposed about the needle;
    an elongate sheath;
    a hub trap comprising first and second arms and a locking structure, the first and second arms being connected to a first end of the sheath, the first and second arms being selectively engageable with the hub; and
    a slider connected to a proximal end of the needle, the slider being disposed about the sheath and movable therealong from a distal position to a proximal position; wherein
    when the slider is in the distal position, the needle extends through and cooperates with the locking structure of the hub trap so as to retain the first and second arms in a closed position wherein the hub is trapped between the first and second arms; and
    when the slider is in the proximal position, a distal tip of the needle is proximal of the locking structure, the first and second arms are in an open position wherein the hub is released from the hub trap, and the needle is disposed entirely within the sheath.

13. The protector of claim 12, wherein when the slider is in the distal position or in any position intermediate the distal position and the proximal position, the needle contacts the arms and provides a force counteracting a spring force biasing the arms toward the open position.

14. The protector of claim 12, wherein when the arms are in the open position, interlocking fingers of the first and second arms block the needle and prevent it from reemerging from the sheath.

15. The protector of claim 12, wherein a stop at a proximal end of the sheath prevents the slider from disengaging the sheath via the proximal end.

16. The protector of claim 12, wherein the slider further comprises a hollow interior chamber in fluid communication with a central lumen of the needle.

17. The protector of claim 16, wherein at least a portion of the slider is transparent and allows viewing of the interior chamber.

18. The protector of claim 12, wherein at least a portion of the sheath is substantially cylindrical.

19. The protector of claim 12, wherein the sheath comprises first and second telescoping members.

20. The protector of claim 12, wherein the hub further comprises a substantially flat fin defining a plane substantially perpendicular to a longitudinal axis of the protector.

* * * * *